United States Patent [19]

Majcherczyk

[11] 4,081,989
[45] Apr. 4, 1978

[54] DEVICE FOR MEASURING THE STRESS OF TANGENTIAL FRICTION OF A SHOE ON A SURFACING FOR THE GROUND

[75] Inventor: Richard Majcherczyk, Boulogne-Billancourt, France

[73] Assignee: Centre Experimental de Recherches et d'Etudes du Batiment et des Travaux Publics, France

[21] Appl. No.: 761,472

[22] Filed: Jan. 24, 1977

[51] Int. Cl.² .......................................... G01N 19/02
[52] U.S. Cl. ............................................ 73/9; 73/105
[58] Field of Search ................................. 73/9, 7, 105

[56] References Cited

U.S. PATENT DOCUMENTS

| 2,225,140 | 12/1940 | Walker | 73/9 |
| 2,955,455 | 10/1960 | Frederik | 73/9 |
| 3,187,552 | 6/1965 | Davies | 73/9 |
| 3,828,605 | 8/1974 | Fazekas | 73/9 |
| 3,975,940 | 8/1976 | Brungraber | 73/9 |

FOREIGN PATENT DOCUMENTS 1,105,319  3/1968  United Kingdom ............ 73/9

Primary Examiner—Richard C. Queisser
Assistant Examiner—Joseph W. Roskos

[57] ABSTRACT

A device for measuring the stress of tangential friction of a shoe on a surfacing for the ground comprises a guiding device, a carriage displaceable over the length of said guiding device, a shoe on said carriage and being subjected to a vertical load dynamometric pick-up means suitable for measuring the tangential friction of the shoe on the surfacing in the course of the displacement of said carriage, a driving assembly for moving the carriage in translation and recorder means connected to the dynamometric pick-up means to record the variation of tangential friction of the shoe on the surfacing.

3 Claims, 6 Drawing Figures

DEVICE FOR MEASURING THE STRESS OF TANGENTIAL FRICTION OF A SHOE ON A SURFACING FOR THE GROUND

The present invention has for object a device for measuring the stress of tangential friction of a shoe on a surfacing for the ground.

It concerns more precisely a device allowing the interpretation by a calculated quantity of the anti-slip qualities of a surfacing for pedestrians.

The putting on the market of a great number of new surfacings makes their selection more difficult, it being given that the data which are provided on their physical qualities and especially on their anti-slip qualities are not complete enough.

Although the slipping of the pedestrian on certain surfacings is a well known phenomenon, the interpretation of this phenomenon by an available calculated quantity is not satisfactory. Indeed, the devices which exist at the present time to measure the anti-slip qualities of a surfacing are incomplete and sometimes even of a debatable principle.

Thus, for example, the Swedes MAYR and CARLSOO have conceived a sort of rigid artificial leg, of regulatable length, supplied with a sliding member, which allows, by the varying of the angle of inclination of this leg, one to determine from what value of the angle slipping of the slipping-member occurs on a given type of surfacing.

These earlier devices have the equal inconvenience of not being able to take into consideration a certain number of factors due to the pedestrian himself, such as for example the angle of attack of the heel relative to the ground.

As a matter of fact it has been determined that during normal walking of a man the angle of attack of the heel relative to the ground lies between 11° and 32° and that certain particular modes of walking are performed with the foot lying flat on the ground and that at variable speeds which can range up to about 7 km/h.

It is known in another connection that the interposition of wax, of a liquid film such as water or oil, or of dusts makes the surfacings more slippery and that the state and the nature of the soles of footwear react in different ways of slipping.

The present invention has then for object a device for the laboratory or for measurement in situ, allowing the avoidance of the aforesaid inconveniences, which simulates the slipping of a pedestrian on a surfacing, the foot lying flat or making a certain angle relative to the direction of displacement.

According to the essential characteristic of the device of the invention, this last comprises in combination:

a guiding arrangement capable of being held parallel to the surfacing, a carriage displaceable in translation for the length of the guiding arrangement, the said carriage being equipped with a shoe subjected to a vertical load and with a dynamometric pick-up suitable for measuring the tangential friction of the shoe on the surfacing in the course of the displacement of the carriage, a driving assembly suitable for drawing the carriage in translation at constant speed over the length of the guiding arrangement, and a recorder connected to the dynamometric pick-up to record the variations of the tangential friction of the shoe on the surfacing in the course of the displacement of the carriage.

The invention will be explained further in detail in the rest of the description which follows with regard to one preferred manner of realisation given solely by way of illustrative example and with reference to the attached drawings in which.

In the figures the same elements are designated by the same numerical references.

Figure 1:
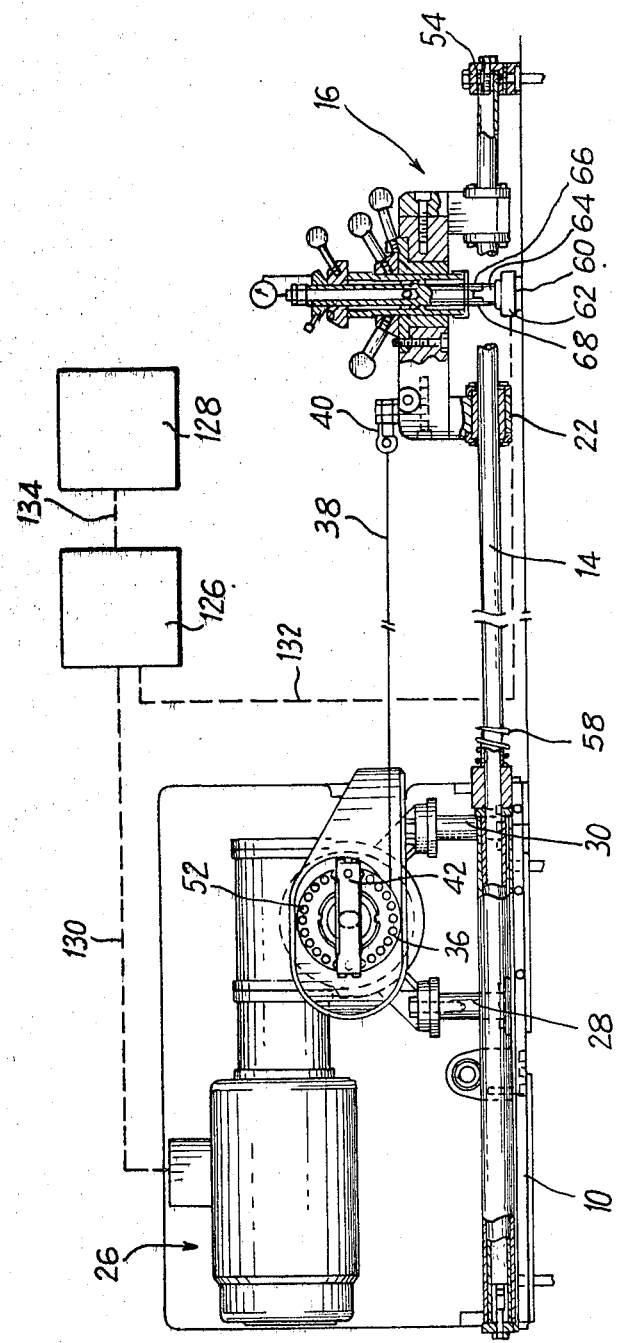
FIG. 1 represents a view in elevation and partly broken away of a device according to the invention.
Figure 2:
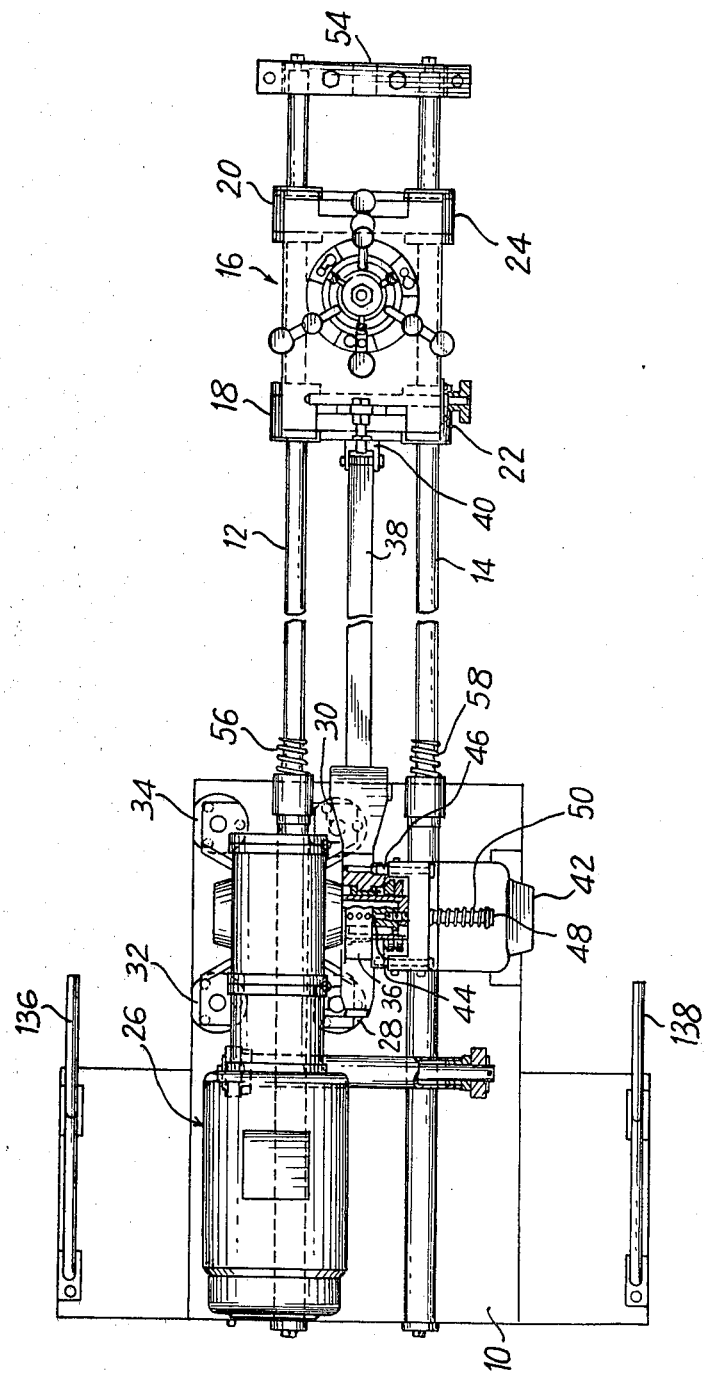
FIG. 2 represents a view from above of the device represented in FIG. 1.

The device represented in FIGS. 1 and 2 comprises a chassis 10 on which are fixed two parallel guiding bars 12 and 14 on which is mounted slidably a carriage 16 by the intermediary of four ball-races 18, 20, 22 and 24 which co-operate two by two with each of the said guiding bars. The carriage 16 can be drawn in translation the length of the guiding device constituted by the bars 12 and 14 by the intermediary of a motor-reducer 26, mounted on the chassis 10 by the intermediary of four fixing feet 28, 30, 32 and 34, driving a pulley 36 on which is wound a ribbon 38 connected to the carriage 16 by a fastening 40. The pulley 36 is provided with a system of manual disconnection in a manner to permit returning the carriage to the position the most removed with respect to the motor-reducer, when one wishes to effect a new measurement. This system of manual disconnection consists of a handle 42 provided with two stops 44 and 46, carried into rotation by the arbor 48 of the motor-reducer and subjected to the action of a spring 50 in such a manner that the stops 44 and 46 co-operate with two orifices diametrically arranged in the side face of the pulley 36 which is mounted for free rotation on the arbor 48. For this purpose the side face of the pulley is provided with a plurality of such orifices 52 (FIG. 1) which thus permit the ensuring of the disconnection of the pulley on the arbor of the motor-reducer for a plurality of fixed positions.

The guiding bars 12 and 14 are connected to one another, at their extremity most removed from the motor-reducer, by a fastening link 54 and are each provided respectively with a buffer spring 56 and 58 so as to brake the carriage 16 at the end of its travel on the guiding arrangement.

The carriage 16 is equipped with a shoe 60 mounted directly on a gauge-pick-up 62 fixed to the lower part 64 of a vertically loaded spindle 66 (FIG. 1). The shoe 60 is intended to rub against the face of the surfacing on which the device of the invention is disposed.

The lower part 64 is articulated on the upper part of the spindle 66 about a pivot 68 parallel to the direction of displacement of the carriage in such a manner that the shoe may follow the irregularities of the surfacing with which it is in contact throughout all the displacement of the carriage.

Figure 6:
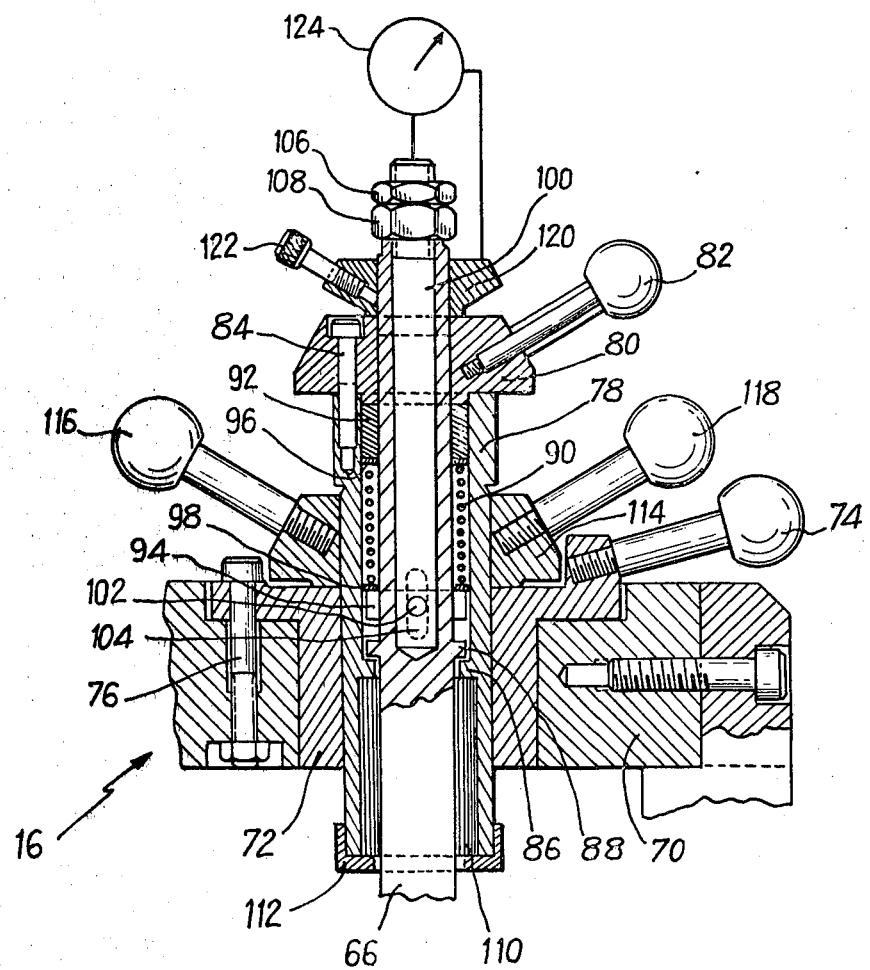
FIG. 6 is an enlarged partial view of FIG. 1 intended to show the carriage of the device better.

The mounting of the spindle 66 on the carriage 16 will be more particularly explained with reference to FIG. 6.

The carriage 16 comprises a block 70 weighing 40 kg. and including a cyclindrical location intended to receive a peg 72 provided with three like handles 74. The peg 72 can be rendered solid with the carriage by means of three like clamp-screw assemblies 76. The peg 72 is screw-threaded interiorly in order to receive a shaft 78 exteriorly screw-threaded and hollow interiorly so as to provide a location for the spindle 66 which supports the shoe. The shaft 78 is provided at its upper part with a tip 80 provided with three like handles 82. The tip 80 is rendered solid with the shaft 78 by means of three screws such as 84. The shaft 78 likewise comprises an annular interior flange 86 which serves as a stop for an annular exterior flange 88 of the spingle 66.

Within the annular spece disposed between the lower part of the tip 80 and the annular flange 88 of the spindle 66 there is a spring 90 held between a distance piece 92 and a base 94 by the intermediary of two slipping washers, 96 and 98. The spring 90 can be calibrated by means of a draw-rod 100, lodged in a cylindrical hollow in the spindle 66, which co-operates with the base 94 through the intermediary of a pin 102 passing through a cylindrical opening arranged in the spindle 66. The position of the draw-rod can be regulated by two nuts 106 and 108 mounted as lock-nuts on the screw-threaded upper extremity of the draw-rod.

The spindle 66 is guided at the base of the shaft 78 by the intermediary of a guiding system of rollers 110 retained by a ring 112.

The shaft 78 is capable of being immobilised in the block 70 by a lock-nut 114 supplied with two handles 116 and 118. In other respects, the spindle 66 is provided with an exterior screw-thread, in the neighbourhood of its upper extremity, which co-operates with a control-ring 120 supplied with three fingers such as 122. Once the spring has been calibrated by means of the draw-pin, the load exercised on the shoe can be made to vary by actuating the control-ring 122.

The load applied on the spindle 66 can be determined by measuring the displacement of the spring by means of a gauge 124 connected on the one hand to the top of the draw-pin and on the other to the ring 120.

The regulation of the load applied to the shoe is effected in the following way:

First the calibration of the spring is regulated by means of the draw-pin; then the position of the shaft on the block of the carriage is regulated so that the shoe comes into contact with the surface of the surfacing, the shoe being correctly orientated; the shaft is locked on the carriage by means of the lock-nut and the control-ring is then activated to modify the applied load, should the occasion arise.

There has also been represented in schematic fashion on FIG. 1 the control-block 126 of the device, as well as the recorder 128 intended to supply a reading of the measurements effected by the gauge-pick-up 62. The control-block is connected by an electric coupling 130 to the motor-reducer 26 and by a flexible electric coupling 132 to the gauge-pick-up 62. This control-block is also connected to the recorder 128 by an electric coupling 134.

The control-block allows the triggering-off of a cycle of measurement while simultaneously setting in motion the motor-reducer and the recorder and the stopping of the cycle of measurement at the end of a pre-determined time while simultaneously stopping the motor-reducer and the recorder.

The drawing-speed of the motor-reducer is pre-set to permit the carriage to attain a constant linear speed, for example of 5 km/h. This recorder is of a classic type allowing the conversion of the data supplied by the gauge-pick-up in a graph representative of the stress of tangential friction of the shoe on the surfacing as a function of time. It can be for example a compact device comprising a supply, a Wheatstone bridge (connected to the resistance of the gauge-pick-up), a hot-wire galvanometer and a device for unrolling paper.

The device of the invention can be used for laboratory tests as well as for tests in situ.

In the laboratory, the device is fixed on a flat bed on which a specimen of surfacing is placed having for example 1.5 m.length by 20 cm. width.

By displacement, the device can be dismantled into three parts; driving assembly, guiding device and carriage. Once mounted on the stand, the device can be displaced by means of three retractable castors (not represented in the figures): two castors fixed under the chassis and a castor fixed under the coupling-bar of the guiding-bars. To facilitate the transport of the device, the latter is supplied with two handles 136 and 138 fixed on the chassis 10 (FIG. 2).

The value measured for the assessment of the anti-slip qualities of a surfacing intended for pedestrians will be the coefficient of friction.

It will be obtained by taking the ratio of the measured tangential stress $F_L$ to the vertical load P $$tg\, \rho = F_L/p$$

The comparison of two coefficients of friction ($tg\, \rho$) should always be made keeping for the tests the same vertical load.

The tests can be carried out on surfaces both dry and wet with water.

However, in very special cases industrial soils for example, the products can be of hydrocarbons, oils etc.

Two distinct coefficients of friction are given by the measurements, the coefficient of friction obtained with the flat shoe on the surfacing ($tg\, \rho_p$), or inclined ($tg\, \rho_i$).

In general a surfacing must be characterised by these two values and the measurements carried out with a sliding member-shoe of rubber. However, according to requirement, the sliding member can be replaced by neoprene, leather or any other similar material.

We will refer now to FIGS. 3 to 6 to describe the manner of fixing of the shoe on the gauge-pick-up.

Figure 3:
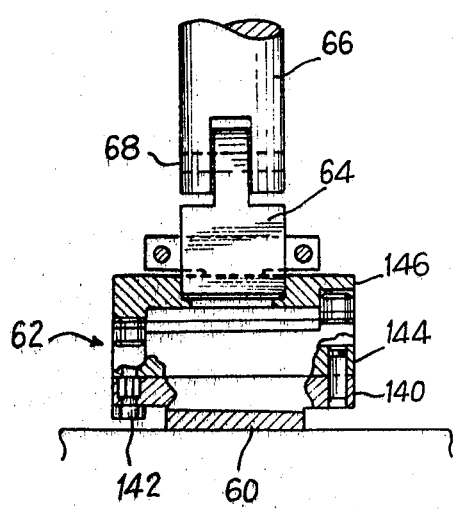
FIG. 3 represents a longitudinal section of a flat shoe suitable for equipping the device of the invention.

There is represented in FIG. 3 a shoe 60 stuck onto a plate 140 which is fixed by the intermediary of screws such as 142 on the lower part 144 of a gauge-pick-up 62. The upper part 146 of this gauge-pick-up is fixed on the lower part 64 articulated on the spindle 66 by the intermediary of the pivot 68. The parts 144 and 146 can slide relative to one another in a direction parallel to the displacement of the carriage so that, when the shoe 60 rubs on a surfacing, these two parts tend to shift relative to one another. This relative movement of the parts 146 and 147 tends to deform the electrical resistance connected to each of these two parts and consequently to make the characteristics of this resistance vary. Variations of this resistance which is connected to the Wheatstone bridge of the recorder are transmitted to the galvanometer of the recorder and registered in continuous fashion on the paper which unrolls from the recorder.

Figure 4:
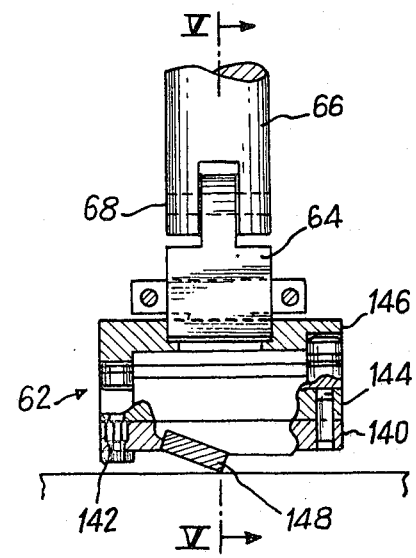
FIG. 4 represents a longitudinal section of an inclined shoe suitable for equipping the device of the invention.

FIG. 4 is identical to FIG. 3, with this exception that the shoe 148 has been mounted at an inclined angle to the plate 140.

Figure 5:
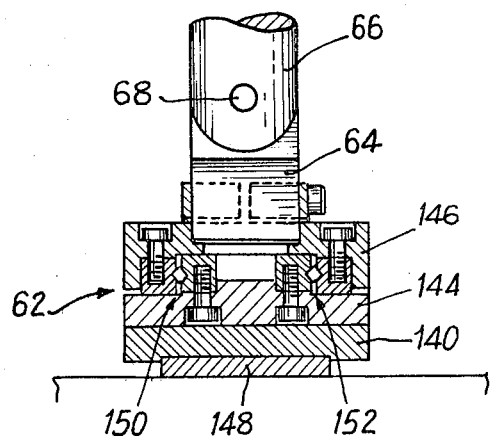
FIG. 5 is a section taken along the line V—V of FIG. 4.

FIG. 5 represents a section along the line V—V of FIG. 4. This figure shows the slicing of the two parts 144 and 146 of the gauge-pick-up 62 by means of two ball grooves 150 and 152 disposed parallelly to the direction of displacement of the carriage.

The shoes used for the flat shoe tests will be for example square shoes of about 4 cm. side, which corresponds to the average surface of the heels of footwear.

In disposing of a plurality of interchangeable plates 140 equipped with shoes either flat or inclined and realised in different materials, one can thus for a given surfacing make a whole series of measurements by varying only the appropriate factors of the shoe.

Although the invention has been described with reference to a particular manner of realisation of the device of the invention, it extends also to the variants of realisation which will appear in an evident manner to the man of the art.

I claim:

1. Device for measuring the stress of tangential friction of a shoe on a surfacing for the ground comprising:
    a guiding device capable of being held parallel to the surfacing,
    a carriage displaceable over the length of the guiding device, a shoe on said carriage, said shoe being subjected to a vertical load,
    dynamometric pick-up means capable of measuring the tangential friction of the shoe on the surfacing in the course of said displacement of said carriage, said shoe being fixed directly on said dynamometric pick-up means, which is mounted at the lower extremity of a loaded vertical spindle mounted slidably on said carriage,
    driving assembly for moving said carriage at constant speed over the length of said guiding device, and
    recorder means connected to the dynamometric pick-up means to record the variations of tangential friction of the shoe on the surfacing in the course of the displacement of said carriage.

2. Device according to claim 1, wherein said spindle is loaded by a calibrated spring the displacement of which is measured to determine the load.

3. Device according to claim 1, wherein the lower part of said spindle is articulated to the upper part of the spindle about a pivot parallel to the direction of the displacement of said carriage.

* * * * *